US010051852B2

(12) United States Patent
Wang et al.

(10) Patent No.: US 10,051,852 B2
(45) Date of Patent: Aug. 21, 2018

(54) FUEL CANISTER AND ADAPTER FOR INSECT REPELLENT DEVICE

(71) Applicant: Thermacell Repellents, Inc., Bedford, MA (US)

(72) Inventors: Wender Wang, Arlington, MA (US); Stephen Shapiro, Bedford, MA (US)

(73) Assignee: Thermacell Repellents, Inc., Bedford, MA (US)

( * ) Notice: Subject to any disclaimer, the term of this patent is extended or adjusted under 35 U.S.C. 154(b) by 0 days.

(21) Appl. No.: 15/439,601

(22) Filed: Feb. 22, 2017

(65) Prior Publication Data

US 2017/0238523 A1    Aug. 24, 2017

Related U.S. Application Data

(60) Provisional application No. 62/298,639, filed on Feb. 23, 2016.

(51) Int. Cl.
| | |
|---|---|
| *A01M 1/20* | (2006.01) |
| *F23D 14/18* | (2006.01) |
| *F23D 14/28* | (2006.01) |
| *F23Q 3/00* | (2006.01) |
| *G05D 16/06* | (2006.01) |
| *A61L 9/03* | (2006.01) |
| *F23C 13/00* | (2006.01) |
| *A01M 29/12* | (2011.01) |

(52) U.S. Cl.
CPC .......... *A01M 1/2088* (2013.01); *A01M 29/12* (2013.01); *A61L 9/03* (2013.01); *F23C 13/00* (2013.01); *F23D 14/18* (2013.01); *F23D 14/28* (2013.01); *F23Q 3/002* (2013.01); *G05D 16/0636* (2013.01); *F23K 2900/05002* (2013.01)

(58) Field of Classification Search
CPC ......... A01M 1/2088; F23C 13/00; A61L 9/03; F23Q 3/002; F23D 14/28; F23D 14/18; G05D 16/0636
See application file for complete search history.

(56) References Cited

U.S. PATENT DOCUMENTS

| | | | | |
|---|---|---|---|---|
| 4,693,868 | A * | 9/1987 | Katsuda | A01M 1/2077 422/124 |
| 4,699,123 | A * | 10/1987 | Zaborowski | A45D 1/02 126/409 |
| 5,476,376 | A | 12/1995 | Santhouse et al. | |
| 5,928,605 | A * | 7/1999 | Bonnema | A01M 1/2088 126/401 |
| 6,503,459 | B1 * | 1/2003 | Leonard | A01M 1/2088 422/120 |
| 7,350,721 | B2 * | 4/2008 | Ghazarian | A61L 9/02 128/203.26 |
| 7,934,495 | B2 * | 5/2011 | Goldenberg | A61K 8/922 126/208 |
| 8,047,837 | B2 * | 11/2011 | Furner | A01M 1/2088 422/125 |

* cited by examiner

*Primary Examiner* — Regina M Yoo
(74) *Attorney, Agent, or Firm* — Levisohn Berger LLP

(57) ABSTRACT

A gas-fueled portable device for the thermal dispensing of volatile materials such as insect repellents is described. The device employs a pressure regulator to establish gas flow, heat generation, and dispensing temperature at pre-determined optimal values. The automatic operation at pre-determined settings provides simple on/off operation for the user of the device.

10 Claims, 5 Drawing Sheets

FUEL CANISTER AND ADAPTER FOR INSECT REPELLENT DEVICE

RELATED APPLICATIONS

This application claims priority of U.S. Provisional Patent Application No. 62/298,639 filed on Feb. 23, 2016, the entire contents of which are incorporated herein by reference.

BACKGROUND OF THE INVENTION

This invention relates to the widespread use of fuel canisters by campers and backpackers and their ability to utilize canisters they carry with them to also power an insect repellent device.

The assignee of the present invention is also the assignee in interest of prior patents relating to controlled fuel gas flow to heat a device for repelling insects and/or powering a portable heating appliance: U.S. Pat. No. 4,733,651; U.S. Pat. No. 4,759,343; U.S. Pat. No. 4,699,123; and U.S. Pat. No. 5,700,430. These prior art appliances contain a fuel supply cartridge which supplies fuel to burners which heat the appliance. The cartridge may contain propane or butane, and often contain a mixture of the two, under sufficient pressure to liquefy the gases. In order to compensate for variations in vapor pressure, which varies with fuel composition and temperature, these prior art devices use pressure regulators to help control gas flow.

During operation, when a cartridge containing the gas fuel is inserted into the appliance, the cartridge valve is not opened and fuel does not flow to the pressure regulator. When the appliance is turned on, the regulator pushes a plunger into the cartridge valve, opening it and allowing gas to flow. When a predetermined pressure is reached, the gas acts upon the diaphragm in the regulator to reduce or stop the gas flow by closing the cartridge valve. Thus, while the part of the regulator that senses pressure is in the appliance, the device that controls gas flow is in the valve built into the cartridge.

There are also numerous camping stoves in the prior art, for cooking and for heating, which rely on gas supplied by canisters but which do not have a pressure regulator. The gas flow in these devices is user-controlled via needle valves. Some stove models do have regulators, but they still have needle valves for user control of the gas flow.

Many campers, RV users, hunters and backpackers who enjoy the outdoors are subject to insect attacks for extended periods of time. The operating times of the insect repellent devices described in the above-listed patents are limited by the amount of fuel in their cartridges. There remains a need for longer term use of insect repellent devices powered by a portable fuel source. There remains also a need for devices that are self-regulating in their fuel flow rate, for reasons of safety and ease of operation.

BRIEF DESCRIPTION

The commonly available larger-capacity fuel canisters may contain propane or butane, and often contain a mixture of the two, under sufficient pressure to liquefy the gases. In order to compensate for variations in vapor pressure, which varies with fuel composition and temperature, the present invention employs a pressure regulator to help finely control gas flow from such canisters.

An important aspect of the present invention is the ability to accurately control fuel flow to the heating element for the insect repellent device. The careful and effective control of fuel flow is an important safety aspect as well as a performance feature of such devices, because the user is generally unable to judge what constitutes an appropriate rate of combustion and rate of insect repellent release. The present invention provides the required precise control, while providing the user with the simplicity and convenience of on/off operation.

Standard fuel canisters come with their own internal valves, but these valves are designed for on/off operation, not for fine flow control. As there are no standards specifying precise dimensions for the valve components, consistent valve control from one brand of canister to another is problematic for an attached appliance. In particular, the degree of control and quality of construction of such valves is not adequate when trying to control gas flow to an insect repellent device. Such devices include a heating plate located beneath an impregnated mat, wherein the heating plate causes the impregnated mat to disperse insect repellent chemicals to provide a reasonably sized insect free area. Proper function depends on heating the impregnated mat to within an appropriate temperature range, and this in turn is highly dependent on the fuel flow rate.

The present invention, which is adapted to be used with standard commercial canisters, shall be described as an insect repellent adapter device (IRAD). The IRAD includes a compact, internal pressure regulator to regulate gas flow, and to thereby maintain and control temperature to heat the plate and heat the mat thereupon to dispense volatile substances impregnated into the mat. The IRAD has a regulator valve that is normally off and when the canister is installed, while a pin in the IRAD presses against and opens the valve in the canister. Initially, the regulator valve in the IRAD blocks gas flow. The internal pressure regulator has a plunger that acts on the regulator valve to open or close the valve. A regulator spring located above the regulator valve acts on a diaphragm to open the regulator valve. Ultimately the device finely controls the amount of gas passing from the canister to the burner to control the temperature of the heating plate and the dispersion of the volatile materials within the mat.

BRIEF DESCRIPTION OF THE DRAWINGS

The invention is shown in greater detail in the following illustrative drawings of which.

DETAILED DESCRIPTION

Figure 1:
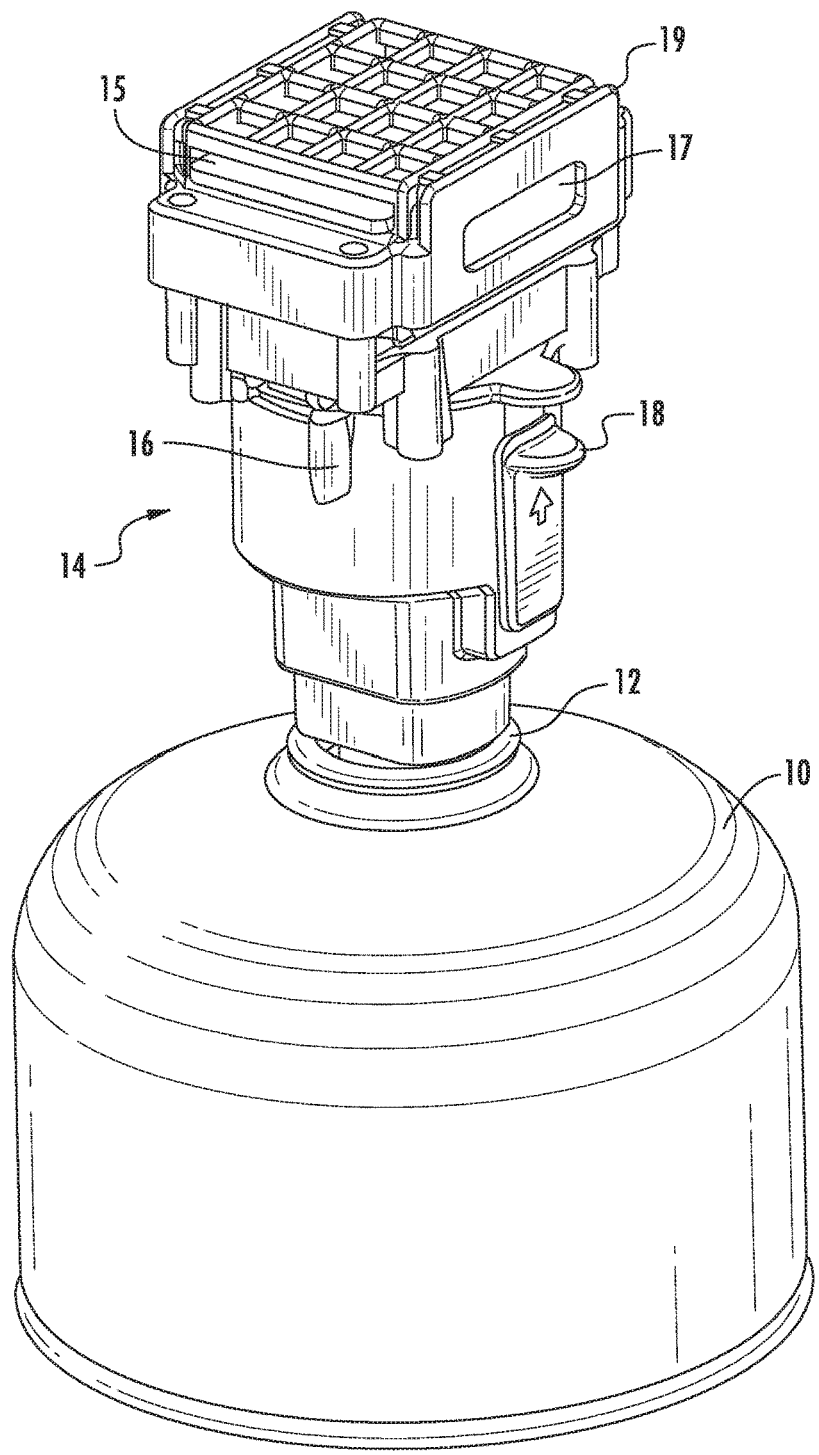
FIG. 1 is a perspective CAD drawing of a traditional fuel canister with the IRAD attached thereto.

The present invention provides a gas-fueled, portable device for dispensing a heat-volatilizable substance. The device comprises a tank connection means to receive a fuel tank or canister. The connection means may comprise a threaded connector that is complimentary to the threads on the fuel tank or canister that one wishes to attach. Alternative connection means may be, for example, quick-connect fittings, including push-to-connect and twist-on couplings, and other fluid connector designs known in the art. Engagement of the tank with the tank connection means establishes a gas-tight connection, and preferably opens a valve in the fuel tank, which admits gaseous fuel into a pressure regulator valve within the device.

The device incorporates a valve switch operably connected to the pressure regulator valve. This valve switch is operable by the user, who can move the valve switch between an on position and an off position, thereby opening or closing the pressure regulator valve. With this single switch, the user can turn the device on or off.

A pressure regulator is in fluid communication with the pressure regulator valve. The pressure regulator is responsive to the gas pressure downstream of the regulator, which biases the regulator toward the valve-closed position. This operates the pressure regulator valve so as to maintain a predetermined gas pressure on the downstream side. This pressure is factory-set, although adjustment is possible via adjustment of a spring that biases the regulator toward the open position.

A fuel combustion means is downstream of and in fluid communication with the pressure regulator. The fuel combustion means may be one or more fuel burner nozzles, which support a flame, or a flameless catalytic burner which catalyzes oxidation of the fuel at a lower temperature than the fuel's ignition temperature.

A sole plate, typically formed from a durable, thermally conductive material such as stainless steel, is in thermal communication with the combustion means. "In thermal communication with" means that the sole plate is fixed above, attached to, or otherwise disposed in sufficient proximity to the combustion means that heat generated by combustion is transferred to the sole plate. The upper surface of the plate constitutes a heated surface upon which the heat-volatilizable substance may be placed. Typically, the volatilizable substance is impregnated into a fibrous or porous mat for ease of handling, and the impregnated mat is placed by the user upon the heated surface.

In operation, the pressure regulator valve meters the flow of the gaseous fuel through the combustion means at a predetermined rate, so as to sustain a predetermined rate of fuel combustion. This in turn heats the sole plate to a predetermined temperature that is sufficient to dispense the heat-volatilizable substance from the heated surface at a predetermined, optimal rate.

Attention is now brought to the drawings, which are CAD drawings showing one particular embodiment of the present invention. Labels identifying each of the parts have been maintained for ease of understanding, in addition to the use of reference numerals.

FIG. 1 shows a traditional fuel canister 10, having a standard top connector 12 attached to an IRAD 14 of the present invention. The IRAD contains an external on/off fuel button 16 which is operably connected to an internal regulator valve. The IRAD 14 has an ignitor button 18 which triggers a piezoelectric ignitor. The IRAD is topped with a combustion chamber 17, contained within protective grille 19, upon which the insect repellent mat 15 rests.

Figure 2:
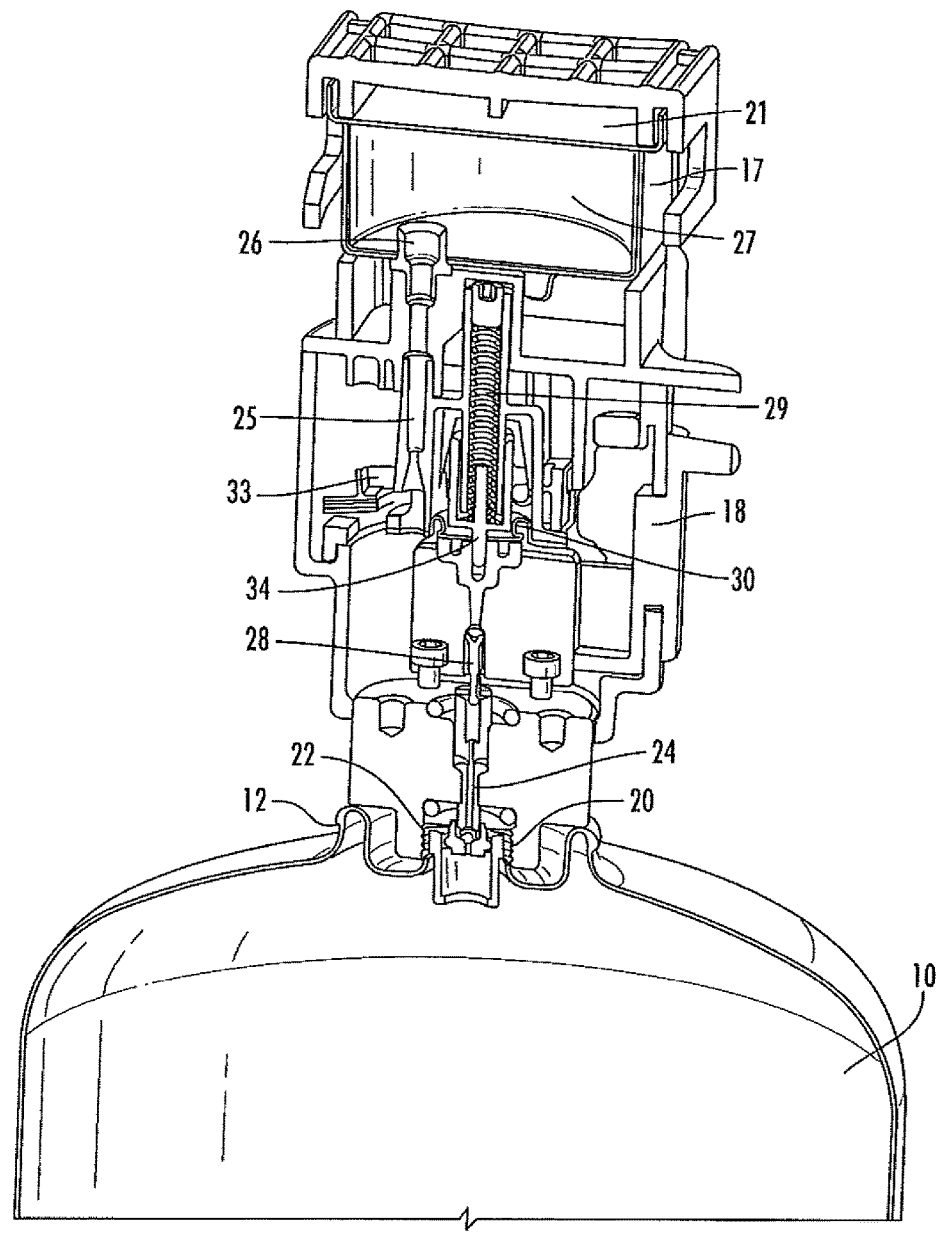
FIG. 2 is an exploded perspective sectional CAD drawing showing the parts of the IRAD connected to and operative with the valve in the canister to control fuel flow to the burner.

FIG. 2 is a breakaway CAD drawing showing the internal parts of the IRAD. The IRAD attaches to the canister connector 12 with canister valve threads 20 engaging complimentary threads 22 at the bottom of the IRAD. In a typical embodiment, the canister valve is of the standard form, e.g. that marketed by the Lindal Group as model B188, having male 7/16 inch UNEF threads, which mate with complimentary female threads 22 on the IRAD 14 of the present invention.

The IRAD includes a pin 24 located at the bottom of the IRAD and projecting therefrom, which is fixedly held to the IRAD and which opens the canister valve when threads 20 and 22 are engaged, allowing fuel to flow through the canister valve and into the IRAD.

The IRAD and pin 24 are related such that the pin defines a vertical axis which centers the various elements which control the flow of fuel from the canister through the IRAD to the gas tube 25, which leads the gas to burner 26. Combustion chamber 17 defines a combustion area 27. Gas combusts within combustion area 27, leading to the heating of heating plate 21. The mat containing the volatile insect repellent rests upon the heating plate.

Figure 5:
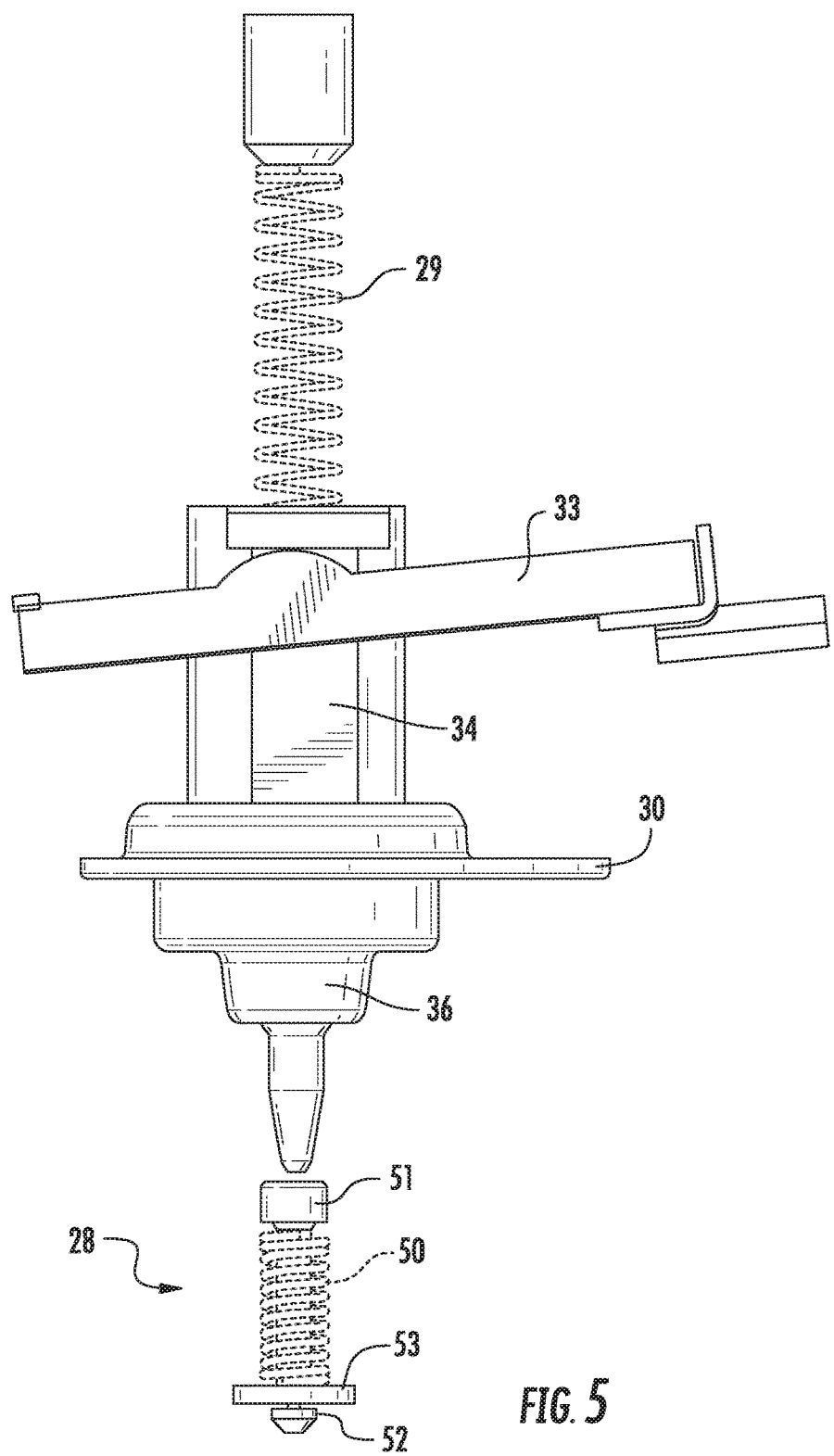
FIG. 5 is a perspective CAD drawing showing components of the pressure regulator.

When the on/off button 16 in the "off" position, regulator valve 28 is held by a valve spring in the closed position, blocking the gas flow (see FIG. 5.) When the on/off button 16 in the "on" position, regulator spring 29 presses down against a plunger stop and plunger, which exert a counterforce that opens regulator valve 28.

Moving the on/off button 16 into the on position lowers lever 33, which releases plunger stop 34, which is biased downward onto plunger 36 by a regulator spring 29. The regulator spring 29 applies pressure to the plunger stop, which in turn presses down on the plunger, which in turn opens regulator valve 28 against the force of the valve spring. Thus, the regulator spring tends to act on the plunger so as to open the regulator valve.

The plunger stop 34 and plunger 36 make contact through a central hole in a flexible diaphragm 30. The lower surface of the regulator diaphragm faces, and is in contact with, the gas flowing from the opened regulator valve. As gas emerges from the regulator valve, it enters a regulated pressure chamber defined, in part, by the lower surface of the regulator diaphragm. The area of contact between the diaphragm and the plunger provides a gas-tight seal, so that gas does not seep between them but is constrained so as to exert pressure against the lower surface of the diaphragm. As the pressure in the regulated pressure chamber rises, it presses against the diaphragm in opposition to the force applied by the regulator spring, allowing the valve spring to close the regulator valve.

In operation, a balance is maintained between the regulator spring, pushing the diaphragm and plunger downward and biasing the regulator valve toward the open position, and the gas pushing against the other side of the diaphragm in the opposite direction, which tends to bias the regulator valve towards the closed position. When these forces are balanced, gas pressure within the regulated pressure chamber is held to a steady level, and gas flow through the gas tube to the burner is thereby controlled without incurring the cost, complexity, and inconvenience of user-operated flow control devices. The user merely has to rotate the on/off button to the "on" position, and proper gas pressure and flow rate are maintained automatically.

Controlling the pressure controls the flow rate of gas to the burner, which translates to control of the amount of heat transferred to the pad and to the mat. This regulation of the heat regulates the temperature of the mat, and dispersion of the volatile substance on the mat is thereby effected in a controlled manner.

When the on/off button 16 is returned to the off position, the plunger stop 34 is lifted by lever 33, which lifts the regulator plunger away from the flow control valve. The flow control valve spring, being unopposed, then closes the regulator valve 28, blocking the gas flow and extinguishing the burner.

Ignition of the gas is preferably accomplished via a piezoelectric igniter, and combustion is carried out in a flame-arresting chamber. One side of the ignition circuit is the burner tube, and the other side is a wire located near the tube, so that a spark jumps between the two when the piezoelectric switch is activated. If gas is flowing through the gas tube and into the burner, the gas is thereby ignited, and heating of the burner and mat begins.

In alternative embodiments, the fuel may be burned by catalytic (flameless) combustion over a ceramic-supported platinum catalyst. The construction and use of gas-fueled catalytic heaters is well-known in the art.

Once combustion has been established, the flame is invisible, but in preferred embodiments the user can confirm normal operation by observing the glowing ignition wire, or the glow of a heated indicator device, through a hole provided in the body of the IRAD for the purpose of such viewing. Alternatively, an LED light powered by a thermoelectric generator (peltier chip) can indicate proper operation.

Figure 3:
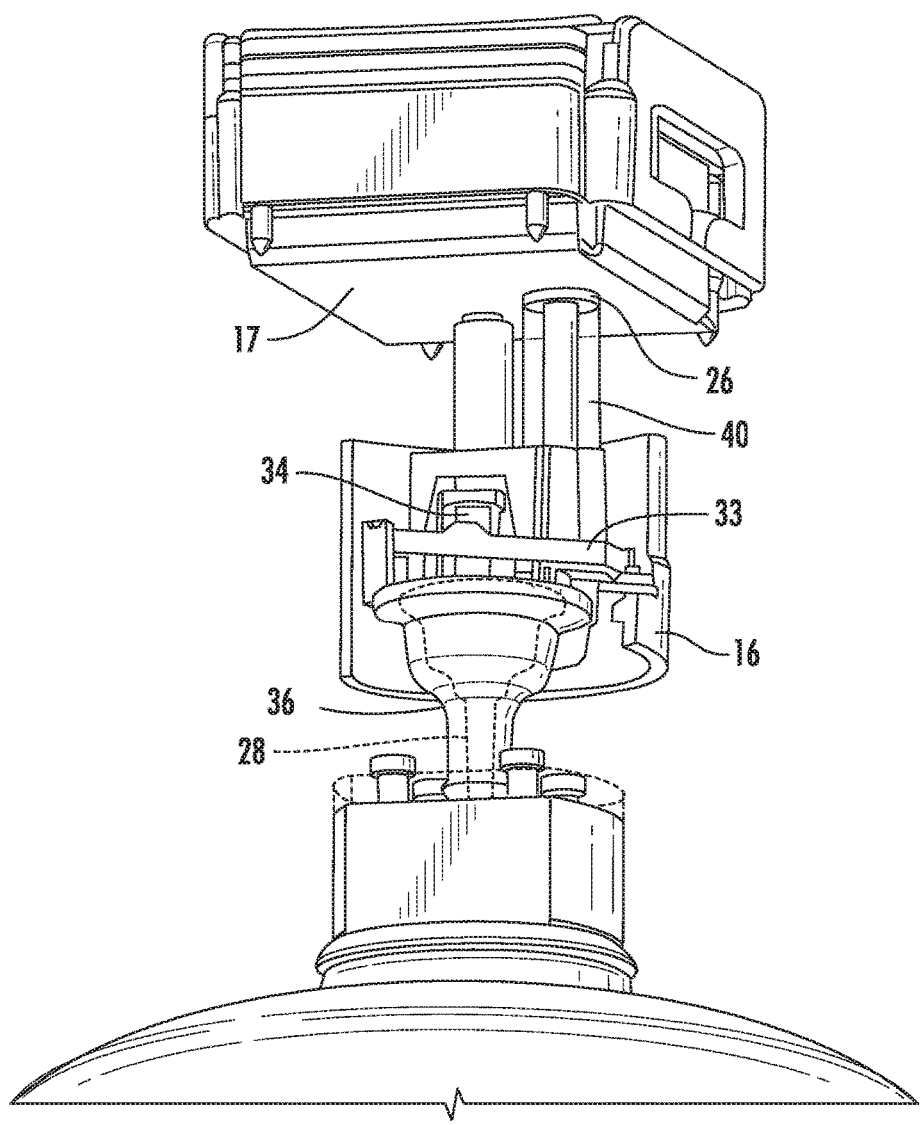
FIG. 3 is another exploded CAD drawing of the interconnection between the IRAD and canister showing additional elements which control the amount of gas flow to the burner.

FIG. 3 is a cutaway perspective view of the above-described components, showing the relationship between the lever 33, shown in the "on" configuration, the plunger stop 34 released by the lever and pressing down upon the diaphragm 30 and plunger 36, and the regulator valve 28 under pressure from the plunger. FIG. 3 also shows an optional flexible tube 40 that leads gas from the gas tube 25 to the burner 26. Suitable alternatives are gas passages molded into or defined by the body 41 of the device, as shown in FIG. 4.

Figure 4:
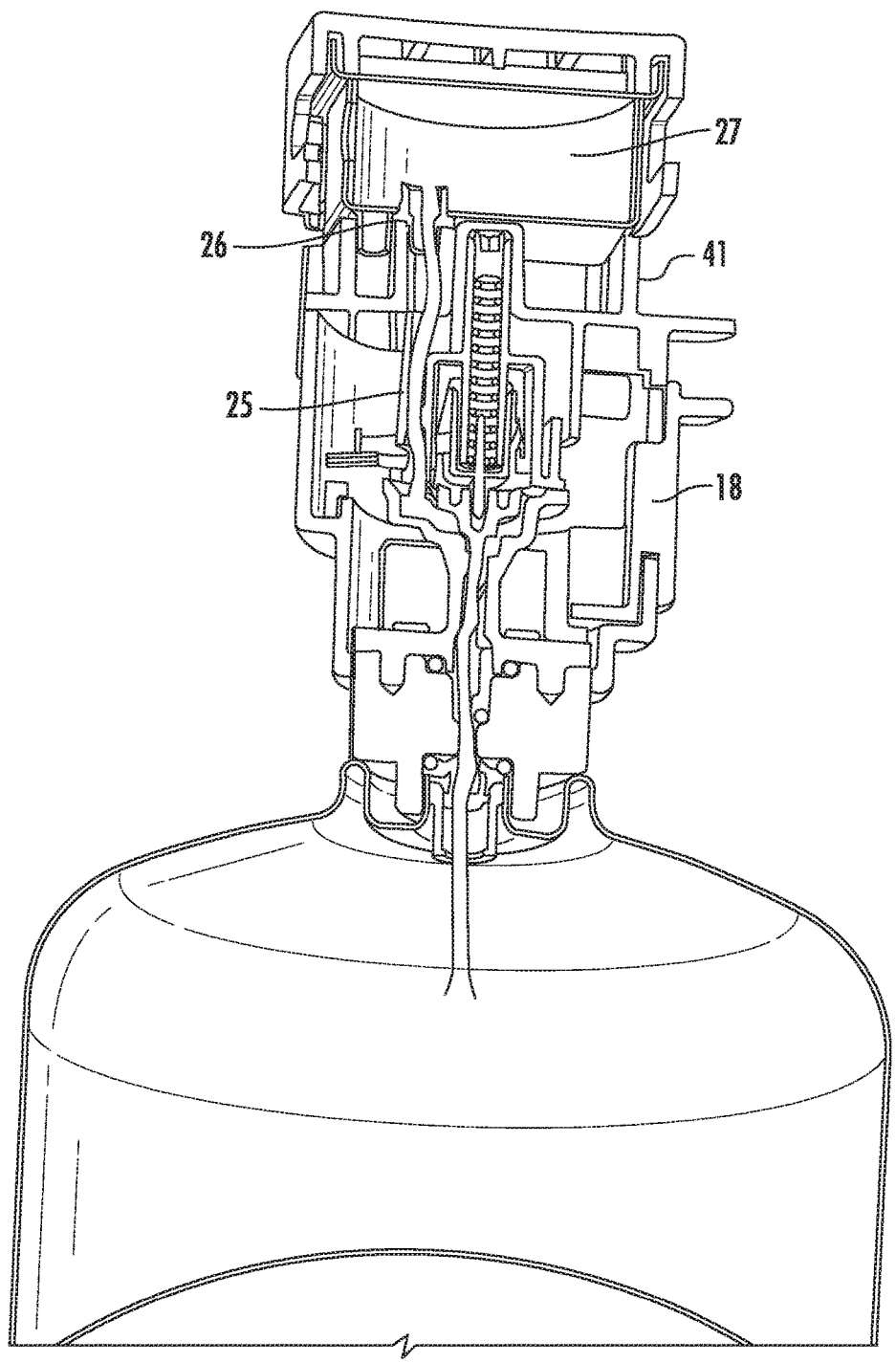
FIG. 4 is a perspective CAD drawing showing the flow of gas from the canister to the burner through the intermediate pressure regulator valve of the IRAD.

FIG. 4 illustrates the path taken by the fuel gas as it passes from the canister to the combustion chamber, when the switch, regulator and valve components are all in the "on" configuration. The gas exits from the regulator valve 28, and passes around the plunger 36 and upward to the gas tube 25, and from there to the burner 26.

FIG. 5 shows the regulator components in the "off" configuration. In this configuration, lever 33 holds plunger stop 34 up, which lifts the plunger away from the flow control valve. The valve spring 50, being thus unopposed, lifts valve pin 51, closing the flow control valve by sealing the pin flange 52 against washer 53.

It should be understood that a preferred embodiment has been described and represented in the drawings so as to provide a clear illustration of the principles of the invention and its practical application, in order to enable one of ordinary skill in the art to make and utilize the invention in various embodiments and with various modifications as may be suitable for the particular use contemplated.

We claim:

1. A gas-fueled, portable device for dispensing a heat-volatilizable substance, comprising
   a. a tank connection means to receive a fuel tank, wherein engagement of the fuel tank with the tank connection means opens a valve in the fuel tank and admits gaseous fuel into a pressure regulator valve, the pressure regulator valve being operable by a movable plunger;
   b. a valve spring biasing the pressure regulator valve toward the closed position, and a regulator spring biasing the movable plunger so as to exert a counter-force that biases the pressure regulator valve toward the open position;
   c. a valve switch having an off position and an on position, operable by a user and operably connected to a lever;
   d. the lever being operably connected to and causing a movement of a plunger stop, the movement of the plunger stop alternately opening and closing the pressure regulator valve upon movement of the valve switch alternately between the on position and the off position;
   e. a pressure regulator in fluid communication with the pressure regulator valve and operating the pressure regulator valve so as to maintain a predetermined gas pressure downstream of the pressure regulator when the pressure regulator valve is open;
   f. a fuel combustion means downstream of and in fluid communication with the pressure regulator; and
   g. a sole plate in thermal communication with the fuel combustion means and having a heated surface for heating the heat-volatilizable substance;
   wherein, when the valve switch is moved to the "off" position, the lever moves the plunger stop against the bias of the regulator spring, thereby allowing the valve spring to move the movable plunger and close the pressure regulator valve, and when the valve switch is moved to the "on" position, the lever moves the plunger stop in the opposite direction, thereby allowing the regulator spring to bias the movable plunger in opposition to the bias of the valve spring; and
   wherein the pressure regulator valve, when open, meters the flow of the gaseous fuel through the fuel combustion means at a predetermined rate, so as to sustain a predetermined rate of fuel combustion which heats the sole plate to a predetermined temperature, the temperature being sufficient to dispense the heat-volatilizable substance from the heated surface.

2. The gas-fueled portable device according to claim 1, wherein the tank connection means comprises female 7/16 inch UNEF threads and is adapted to operably connect the device to a fuel tank having a Linda' model B188 valve.

3. The gas-fueled portable device according to claim 2, wherein the fuel combustion means is a fuel nozzle adapted to support a flame.

4. The gas-fueled portable device according to claim 3, further comprising a piezoelectric fuel igniter.

5. The gas-fueled portable device according to claim 2, further comprising a piezoelectric fuel igniter.

6. The gas-fueled portable device according to claim 2, wherein the fuel combustion means is a catalytic burner.

7. The gas-fueled portable device according to claim 1, wherein the fuel combustion means is a fuel nozzle adapted to support a flame.

8. The gas-fueled portable device according to claim 7, further comprising a piezoelectric fuel igniter.

9. The gas-fueled portable device according to claim 1, further comprising a piezoelectric fuel igniter.

10. The gas-fueled portable device according to claim 1, wherein the fuel combustion means is a catalytic burner.

* * * * *